United States Patent [19]
McDaniel et al.

[11] Patent Number: 5,885,295
[45] Date of Patent: Mar. 23, 1999

[54] APPARATUS AND METHOD FOR POSITIONING AN ORTHOPEDIC IMPLANT

[75] Inventors: John McDaniel, Bloomington; Merrill Ritter, Indianapolis, both of Ind.

[73] Assignee: Biomet, Inc., Warsaw, Ind.

[21] Appl. No.: 693,416

[22] Filed: Aug. 7, 1996

[51] Int. Cl.⁶ ........................................................ A61F 2/46
[52] U.S. Cl. ................................ 606/86; 606/85; 606/89; 606/95; 606/99
[58] Field of Search .................................. 606/84, 85, 86, 606/87, 89, 95, 99

[56] References Cited

U.S. PATENT DOCUMENTS

| | | |
|---|---|---|
| 4,357,716 | 11/1982 | Brown . |
| 4,404,692 | 9/1983 | Eftekhar . |
| 4,523,587 | 6/1985 | Frey . |
| 4,559,936 | 12/1985 | Hill . |
| 4,657,549 | 4/1987 | Keller . |
| 4,718,909 | 1/1988 | Brown . |
| 4,827,919 | 5/1989 | Barbarito et al. . |
| 4,919,679 | 4/1990 | Averill et al. . |
| 4,997,448 | 3/1991 | Filer . |
| 5,002,580 | 3/1991 | Noble et al. . |
| 5,041,141 | 8/1991 | Ypma et al. . |
| 5,062,854 | 11/1991 | Noble et al. . |
| 5,078,746 | 1/1992 | Garner . |
| 5,089,004 | 2/1992 | Averill et al. ............................ 606/89 |
| 5,116,380 | 5/1992 | Hewka et al. . |
| 5,127,920 | 7/1992 | MacArthur . |
| 5,147,408 | 9/1992 | Noble et al. . |
| 5,169,401 | 12/1992 | Lester et al. . |
| 5,171,289 | 12/1992 | Tornier . |
| 5,234,432 | 8/1993 | Brown . |
| 5,263,991 | 11/1993 | Wiley et al. . |
| 5,340,362 | 8/1994 | Carbone . |
| 5,342,366 | 8/1994 | Whiteside et al. . |
| 5,514,136 | 5/1996 | Richelsoph ............................... 606/86 |
| 5,569,255 | 10/1996 | Burke ........................................ 606/89 |

OTHER PUBLICATIONS

Kirschner Merdical Corporation, David J. Schurman, M.D. Professor, Jack M. Bert, M.D. Associate Clinical Professor, and Dennis Carter, Ph.D. Professor, *Surgical Techniques C–2® OsteoCap™ Hip*, pp. 1–20.

*Primary Examiner*—Michael Buiz
*Assistant Examiner*—Julian W. Woo
*Attorney, Agent, or Firm*—Harness, Dickey & Pierce, P.L.C.

[57] ABSTRACT

An apparatus and method for positioning an orthopedic implant within a cavity in a bone, including a plug member which is inserted into the cavity in the bone. A cutter movably engages the plug member and is used to create a first mating surface in the bone. A positioning jig having a second mating surface which is adapted to substantially mate with the first mating surface and a third surface adapted to removably engage the orthopedic implant is used to center the orthopedic implant within the cavity in the bone. Upon the second mating surface of the positioning jig mating with the first mating surface within the bone and the third surface removably engaging the orthopedic implant, the orthopedic implant is substantially centrally positioned within the cavity of the bone.

20 Claims, 4 Drawing Sheets

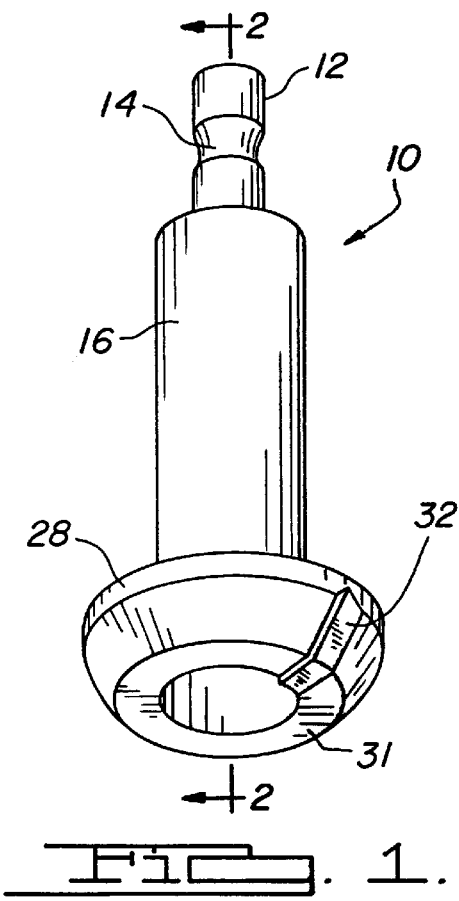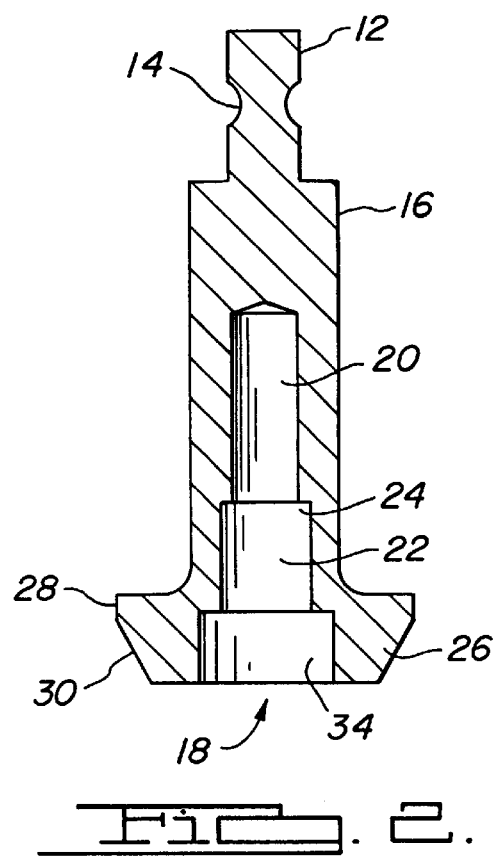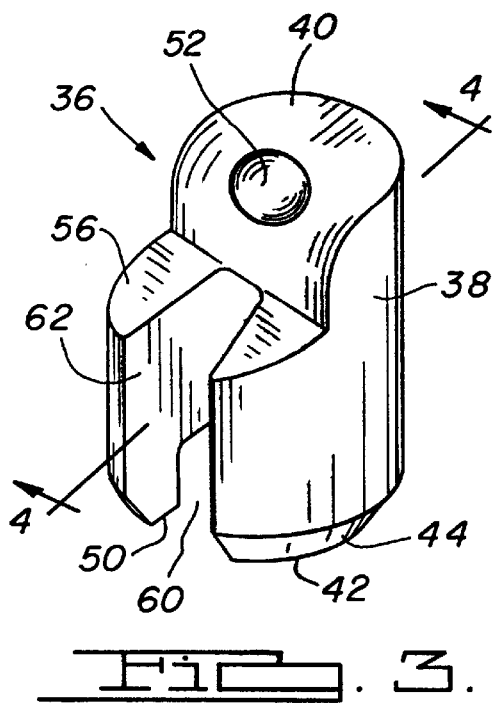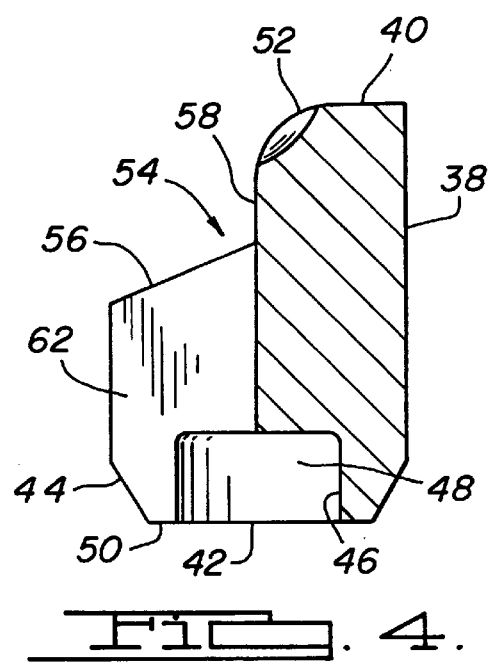

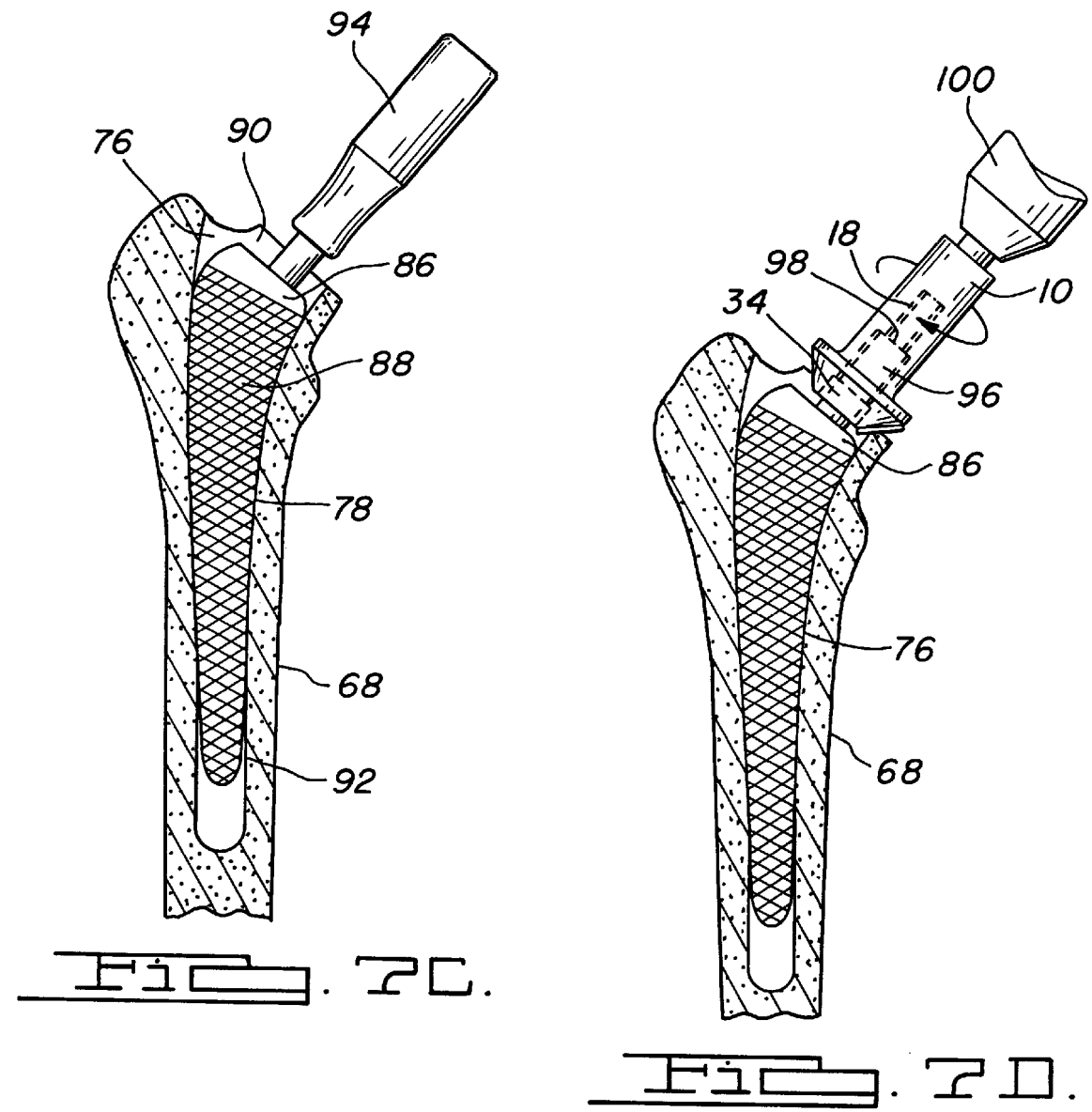
FIG. 7C.
FIG. 7D.
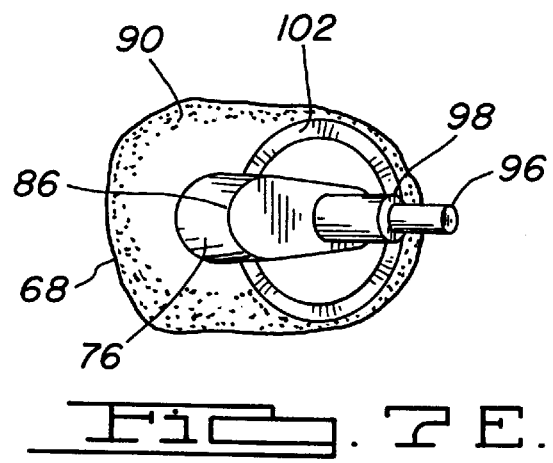
FIG. 7E.

APPARATUS AND METHOD FOR POSITIONING AN ORTHOPEDIC IMPLANT

BACKGROUND OF THE INVENTION

1. Field of the Invention

This invention relates generally to an apparatus and method for use in orthopedic surgery and, more particularly, to an apparatus and method for positioning an orthopedic implant in a cavity in an intramedullary canal.

2. Discussion of the Related Art

A natural hip joint may undergo degenerative changes due to a variety of etiologies. When these degenerative changes become so far advanced and irreversible, it may ultimately become necessary to replace the natural hip joint with a prosthetic hip. When implantation of such a hip joint prosthesis becomes necessary, the head of the natural femur is first resected and a cavity is created within the intramedullary canal of the host femur for accepting the prosthetic hip. If the acetabulum also needs repair, all remnants of articular cartilage are removed from the acetabulum and a cup which will accommodate the head or ball of the prosthetic hip may be affixed to the acetabulum by means of cement, screws or other appropriate fixation means. The hip prosthesis may be inserted and supported within the host femur using generally one of two techniques.

These techniques either involve cementing the hip prosthesis within the host femur or using a non-cementing technique which generally uses a hip prosthesis which snugly fits within and is supported by the host femur.

When utilizing the cementing technique, it is generally desirable to position the hip prosthesis within the cavity made in the intramedullary canal so that a desired cement mantel is formed about the hip prosthesis. By providing a desirable cement mantel, this generally ensures that there are no regions within the cement mantel which may cause stress risers that may lead to subsequent fractures of the cement in these areas. If the hip prosthesis is not located in the desired position, the hip prosthesis may cause abnormal stress to the cement mantel and thereby lead to loosening of the hip prosthesis and the need for revision of the prosthetic hip. Various methods of positioning the prosthetic hip are known and used in the art. However, use of these various methods and techniques sometimes have several disadvantages.

For example, one method of positioning the hip prosthesis is to use a pair of sleeves made of high density polyethylene or polymethyl methacrylate for distal and proximal centering of the hip prosthesis within the cement mantel. One sleeve is positioned at the distal end of the hip prosthesis and the other sleeve is positioned at the proximal end of the hip prosthesis, thereby centering the hip prosthesis within the intramedullary canal. However, the disadvantage with this type of centering technique is that the distal and proximal sleeves are left in place as the cement hardens and may thus create stress risers in the cement mantel at these locations. The stress riser can be much more prominent in the proximal sleeve because this sleeve is generally larger than the distal sleeve.

Another centering method used incorporates a series of small bosses or pegs positioned about and integral with the periphery of the hip prosthesis at the distal and proximal portions. The bosses are used to center the hip prosthesis within the intramedullary canal similar to the sleeves. This technique, however, can also create stress risers in the cement mantel about the distal and proximal bosses.

An additional method utilizes a provisional prosthesis that carries a thumb screw. The thumb screw passes through the lateral portion of the provisional prosthesis and is used to engage the medial wall of the intramedullary canal. The provisional prosthesis is laterally centered within the intramedullary canal by appropriately adjusting the thumb screw. A transverse hole is then created in the host femur and a pin is inserted as close to the provisional prosthesis as possible. This pin is used to prevent the actual hip prosthesis from drifting medially as the implant is placed into the intramedullary canal. The disadvantages of this method are that it only provides control and centering in one direction or axis and may create a small stress riser in the cement mantel when the pin is subsequently removed after the bone cement is cured.

Still another method of positioning the hip prosthesis utilizes an integral collar positioned at the proximal end of the hip prosthesis. The collar nests with the calcar portion of the host femur that is exposed by resection of the head portion of the host femur. However, the integral collar hip prosthesis is generally more difficult to manufacture and therefore is more expensive to utilize than a collarless hip prosthesis.

What is needed then is an apparatus and method for positioning an orthopedic implant which does not suffer from the above mentioned disadvantages. This in turn, will help provide a desirable cement mantel about the orthopedic implant, reduce the number of possible stress risers within the cement mantel, provide implant positioning about multiple axes, reduce the amount of bone material removed from the host bone, and promote the use of lower cost implants, where appropriate. It is, therefore, an object of the present invention to provide such an apparatus and method for positioning an orthopedic implant.

SUMMARY OF THE INVENTION

In accordance with the teachings of the present invention, an apparatus and method for positioning an orthopedic implant is disclosed. The apparatus and method locates the orthopedic implant within a cavity formed in a bone so that a desirable cement mantel may be formed about the orthopedic implant. This is basically achieved by utilizing a removable positioning jig that engages the orthopedic implant and includes a surface that mates with a surface formed in the bone adjacent to the cavity in the bone.

In one preferred embodiment, a set of surgical instruments are used for positioning a hip prosthesis in a cavity of an intramedullary canal of a host femur. The set of surgical instruments includes a plug member that is inserted into the cavity of the intramedullary canal. A cutter engages the plug member to create a first mating surface in the host femur. A positioning jig includes a second mating surface that substantially mates with the first mating surface in the host femur and a third surface that removably engages the hip prosthesis. Upon the second surface substantially mating with the first surface and the third surface removably engaging the hip prosthesis, the hip prosthesis is positioned within the cavity of the intramedullary canal of the host femur.

Use of the present invention provides an apparatus and method for positioning an orthopedic implant in a cavity formed in a bone. As a result, the aforementioned disadvantages associated with the currently available methods and techniques for positioning orthopedic implants have been substantially reduced or eliminated.

BRIEF DESCRIPTION OF THE DRAWINGS still other advantages of the present invention will become apparent to those skilled in the art after reading the following specification and by reference to the drawings in which:

FIG. 1 is a perspective view of a cutter according to the teachings of the preferred embodiment of the present invention;

FIG. 2 is a cross-sectional view of the cutter shown in FIG. 1 taken along line 2—2 of FIG. 1;

FIG. 3 is a perspective view of a positioning jig according to the teachings of the preferred embodiment of the present invention;

FIG. 4 is a side cross-sectional view of the positioning jig shown in FIG. 3 taken along line 4—4 of FIG. 3;

FIGS. 7A–7G illustrate a method for positioning an orthopedic implant according to the teachings of the preferred embodiment of the present invention.

DETAILED DESCRIPTION OF THE PREFERRED EMBODIMENT(S)

Figure 5:
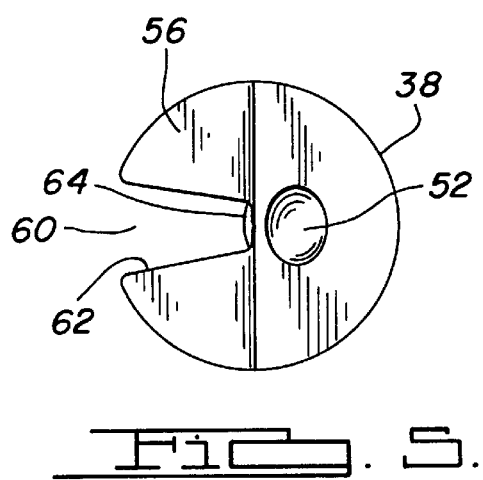
FIG. 5 is a top view of the positioning jig shown in FIG. 3.

The following description of the preferred embodiments concerning an apparatus and method for positioning an orthopedic implant are merely exemplary in nature and are in no way intended to limit the invention or its application or uses. Moreover, while the present invention is described in detail below with reference to performing implantation of a hip prosthesis, it will be appreciated by those skilled in the art that the present invention is clearly not limited to a hip prosthesis and may be utilized with various other orthopedic implants.

Referring to FIGS. 1–2, a cutter 10 according to a preferred embodiment of the present invention is shown. Cutter 10 includes a cylindrical driving shaft 12 having a notch portion 14 which is adapted to be engaged by a conventional driving device such that the cutter 10 can be axially rotated at about 400 rpm. The driving shaft 12 can also be configured to operate with a quick-disconnect device, various conventional chucks such as those sold under the Jacobs trademark, and various conventional shanks such as those sold under the Hudson-Zimmer trademark or other appropriate configuration as known to those skilled in the art. The driving device may be either a conventional power driven device or a conventional hand driven device. Concentric with the driving shaft 12 is an axially extending cylindrical body 16 which defines an axially extending cylindrical bore 18 shown clearly in FIG. 2. The cylindrical bore 18 includes an upper bore portion 20 which has a smaller diameter than a lower bore portion 22. Located within the cylindrical bore 18 is a ledge 24. While the cylindrical bore 18 is shown with the upper and lower bore portions 20 and 22, respectively, one skilled in the art would realize that the cylindrical bore 18 can also be configured in numerous ways, including having a single diameter bore 18.

Positioned concentric with the cylindrical body 16 and laterally extending out from the cylindrical body 16 is a cutting member 26. The cutter member 26 includes a cylindrical ring portion 28, a tapered cutting portion 30, and a planar annual cutting portion 31. The tapered cutting portion 30 and the planar annular cutting portion 31 utilizes a single edge cutter 32 to form or establish a first mating surface or landmark in a bone corresponding to the shape of the tapered cutting portion 30 and the planar annular cutting portion 31. While only a single shape for the tapered cutting portion 30 and the planar annular cutting portion 31 is shown which establishes a corresponding first mating surface or landmark, those skilled in the art would readily recognize that numerous other shapes may be defined using various shaped cutting portions. Passing axially through the cutting member 26 is a cutting bore 34 which is concentric with the cylindrical bore 18. The cutting bore 34 and the cylindrical bore 18 pass through and engage a reference member, further described herein, as the first mating surface is being formed.

Turning to FIGS. 3–6, a positioning jig 36 according to a preferred embodiment of the present invention is shown. The positioning jig 36 has a cylindrical body 38 having a first end 40 and a second end 42. Located at the second end 42 is a second tapered mating surface 44 that corresponds to the first mating surface or landmark formed in the bone using the tapered cutting portion 30 of the cutter 10. The second mating surface 44 includes an internal cylindrical wall 46 which defines a cylindrical bore 48 and an annular seat 50, shown clearly in FIG. 4. Located at the first end 40 of the positioning jig 36 is an arcuate nesting surface 52 which is operable to engage and nest with a head portion of a hip prosthesis, further described herein. Extending centrally and axially from the nesting surface 52 is a notched region 54. The notched region 54 is defined by a 45° wall 56 and 90° wall 58.

Figure 6:
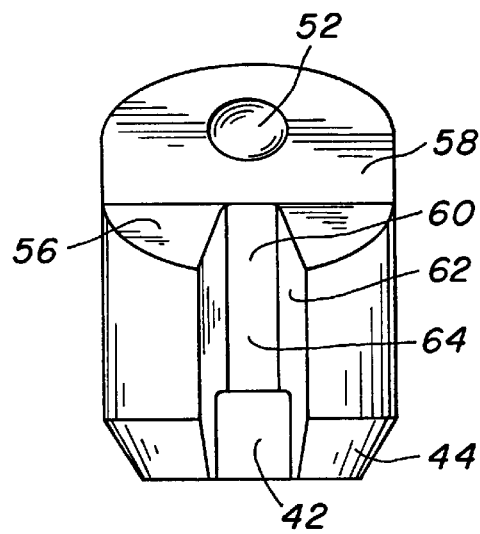
FIG. 6 is a front view of the positioning jig shown in FIG. 3.

Passing axially between the first end 40 and the second end 42 is a "V" shaped slot 60, shown clearly in FIGS. 5 and 6. The "V" shaped slot 60 is defined by tapered sidewalls 62 and an arcuate backwall 64 (see FIG. 5). The "V" shaped slot 60 is used to removably engage a neck portion of the hip prosthesis, further described herein. One skilled in the art will also recognize that various other uniquely shaped slots can be utilized which conform to correspondingly shaped neck portions. The positional relationship between the second mating surface 44 and the surface of the "V" shaped slot 60 is fixed such that upon locating the second mating surface 44 with the first mating surface or landmark formed in the bone and removably engaging the slot 60 of the positioning jig 36 with the hip prosthesis, the hip prosthesis will be located in a predetermined desired position relative to the bone, further described herein.

The method of implanting an orthopedic implant such as a hip prosthesis, which is well known in the art, will now be described utilizing the cutter 10 and the positioning jig 36 with reference to FIGS. 7A–7G. Once a radiograph or x-ray has been taken of the hip that is to be replaced, a suitable acetabular component, as is well known in the art, is selected which may involve the use of a suitably sized template as is also known in the art. If such a template is used, the surface of the acetabular component is placed concentrically with the subchondral bone. Once the acetabular component is chosen, a proper sized hip prosthesis is chosen to fit within a cavity formed in the intramedullary canal of the host femur using suitably sized templates, also known in the art, or during the operating procedure itself. Based upon the size of the hip prosthesis selected, the surgeon can also then determine the size and the depth of the cavity to be formed within the intramedullary canal.

Figure 7A:
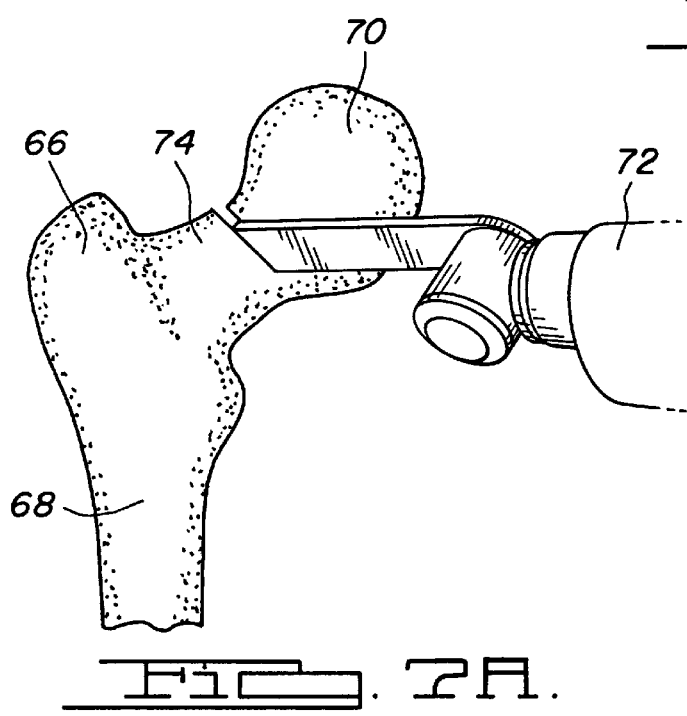

Once the proper acetabular component and the hip prosthesis have been selected, a conventional Steinmann pin is placed over the iliac wing above the acetabular. The Steinmann pin is bent so that it can be used to mark a position on the greater trochanter 66 of the host femur 68. After the hip is dislocated, the head 70 of the host femur 68 is resected using a saw 72 such that a portion of the neck 74 of the host femur 68 is retained, as shown in FIG. 7A. A conventional resection overlay or guide known in the art can be used to estimate the angle and position of the osteotomy by making a mark on the host femur 68.

Once the head 70 is resected, the acetabular component is implanted in a manner known in the art. In this regard, a partial superior and anterior capsulotomy is performed to allow exposure of the anterior acetabular rim in a conventional manner. The acetabulum is then reamed with the largest reamer that easily fits within the acetabulum and is continued until concentric removal of all the remaining acetabular cartilage and the exposure of the punctate bleeding of the subchondral plate is achieved. A conventional metal frame shell gauge corresponding to the last reamer used is then inserted into the acetabulum. The appropriate component position is then judged using a downsized acetabular gauge, also known in the art, which can be easily inserted and positioned in the acetabulum allowing removal of any overhanging anterior, posterior or superior osteophytes. The acetabular shell is locked onto the acetabular positioner and driven into the fully seated position. When located in this manner, it should not be possible to twist the acetabular shell within the bone with the acetabular positioner. If screws are then used to supplement fixation, they should be placed in the region so as to avoid inadvertent protrusion of the screws.

Figure 7B:
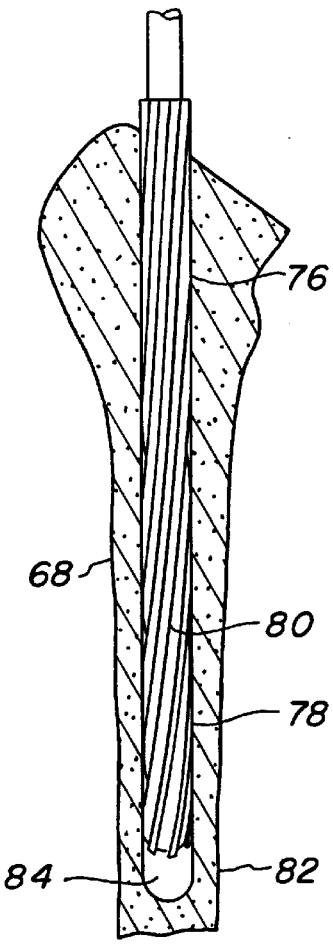

Once the acetabular component is secured and the host femur 68 has been resected in the manner described above or by another suitable manner known in the art, a cavity 76 is initially formed in the intramedullary canal 78 using a reamer 80, shown in FIG. 7B. The distal canal reamer 80 forms a portion of the cavity 76 and shapes of the distal end of the cavity 76. The distal canal reamer 80 reams the intramedullary canal 78 until the hard cortical bone 82 is contacted at the distal end of the diaphyseal cavity 84.

Once the reamer 80 has been removed from the cavity 76, a series of rasps is then used to continue the formation of the cavity 76. The series of rasps starts with a first smaller sized rasp and sequentially moves up to larger sized rasps, ending with the rasp 86. The rasp 86, as well as the smaller rasps employ teeth 88 which cut through the hard calcar bone 90 and the soft cancellous bone 92 within the host femur 68. The rasps may or may not include teeth 88 at the distal end of the rasps. The rasp 86 shapes the cavity 76 to be at least one size larger than the hip prosthesis used. This larger size accommodates for cementing the hip prosthesis within the cavity 76.

Upon forming and defining the cavity 76, a handle 94 of the rasp 86 is removed to expose a cylindrical reference or finger member 96 having a ledge 98 (see FIG. 7E). The cylindrical bore 18 and the cutting bore 34 of the cutter 10 pass over and are operable to rotatably engage the reference member 96 and the ledge 98. With the rasp 86 properly seated within the cavity 76, the cutter 10 is rotated at about 400 rpm using a driving device 100. The cutter 10 is then axially driven downward as the reference member 96 passes through the cutting bore 34 and engages the cylindrical bore 18. Upon the cylindrical bore 18 fully seating atop the reference member 96, the ledge 98 engages the ledge 24 and the first mating surface or landmark 102 is established in the calcar femoral portion 90 of the neck 74. By bottoming out the cutter 10 until the ledge 98 engages the ledge 24, a predetermined depth for the first mating surface 102 is established. Alternatively, if the cylindrical bore 18 has a single diameter bore 18, the distal end of the reference member 96 will bottom out at the distal end of the bore 18.

It should be noted that while the rasp 86 is shown inserted into the cavity 76 and used to guide the cutter 10, those skilled in the art would understand that other types of plug members which can be seated within the cavity 76 may also be utilized such as a provisional prosthesis having the reference member 96. Moreover, while the reference member 96 is discussed in connection with the rasp 86, the geometry may simply be reversed such that the reference member 96 extends out from the cutter 10 and is slidably inserted into a cylindrical groove formed within the rasp 86.

Once the first mating surface or landmark 102 is established in the calcar femoral 90, shown clearly in FIG. 7E, the rasp 86 is removed from the cavity 76. The cavity 76 is then cleaned and dried using compressed air in preparation for cementing.

Once the cavity 76 is cleared of debris and dried, a bone plug 104 is inserted within the distal end of the diaphyseal cavity 84. The bone plug 104 may be of any suitable bone plug known in art such as that disclosed in U.S. Pat. No. 5,263,991, which is hereby incorporated by reference. After the bone plug 104 is positioned in place, the cavity 76 is filled with any suitable grouting material 106. This grouting material 106 may consist of bone cement, resorbable bone cement or morselized bone graft material.

Figure 7F:
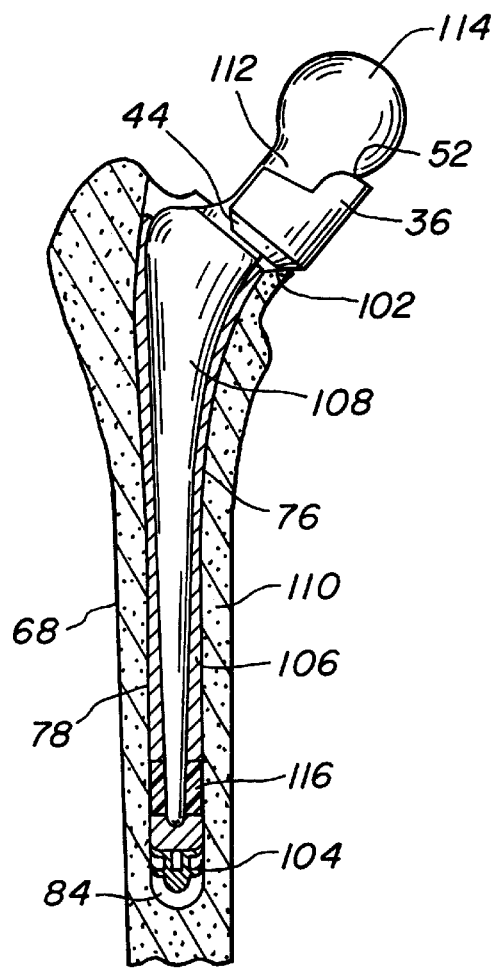
Figure 7G:
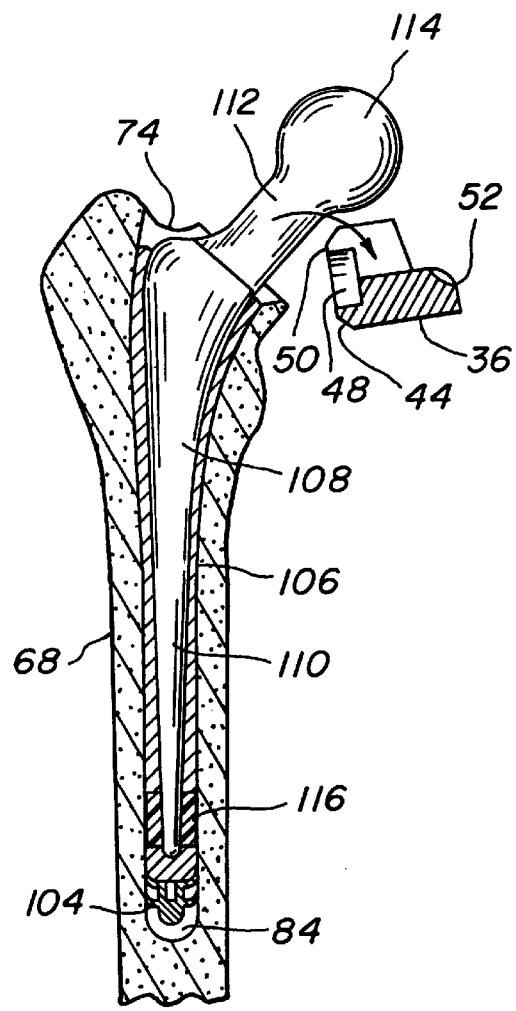

Referring to FIGS. 7F–7G, a hip prosthesis 108 is shown inserted into the cavity 76. The hip prosthesis 108 includes a stem 110, a neck 112 and an integral head 114. The hip prosthesis 108 may consist of a Biomet Model No. 175690 hip prosthesis 108. However, other suitable hip prosthesis may also be utilized including versions that do not include an integral head 114. The hip prosthesis 108 is shown with an optional distal centralizer sleeve 116 positioned about the distal end of the stem 110. The sleeve 116 is used to position the distal end of the stem 110 substantially central within the distal end of the cavity 76.

Prior to inserting the stem portion 110 of the hip prosthesis 108 into the cavity 76 within the intramedullary canal 78, the positioning jig 36 is removably engaged with the hip prosthesis 108. The surface of the "V" shaped slot 60 removably engages the neck 112, and a portion of the integral head 114 nests within the arcuate nesting surface 52. As the stem portion 110 is inserted into the cavity 76, the positioning jig 36 is held in place by the surgeon. During insertion of the stem 110 into the cavity 76, the excess grouting material 106 is forced out of the cavity 76 until the second mating surface 44 mates with the first mating surface or landmark 102 formed in the calcar femoral portion 90 of the host femur 68.

Upon mating the second mating surface 44 with the first mating surface 102, the hip prosthesis 108 is retained in a predetermined position relative to the host femur 68. This enables the hip prosthesis 108 to be secured centrally within the cavity 76, thereby creating a uniform cement or grouting mantel about the hip prosthesis 108. Moreover, the depth of insertion of the hip prosthesis 108 within the cavity 76 is also controllably maintained by use of the positioning jig 36, since the head 114 nests within the nesting surface 52 to retain the hip prosthesis 108 at the proper depth. Therefore, the positioning jig 36 provides triaxial, x-axis, y-axis, and z-axis positioning of the hip prosthesis 108.

The positioning jig 36 is held in place by the surgeon until the grouting material 106 appropriately sets up to retain the hip prosthesis 108 within the cavity 76. Because the positioning jig 36 includes the cylindrical bore 48 and the annular seat 50 adjacent to the second mating surface 44, the positioning jig 36 is able to be held in place without becoming secured within the grouting material 106. That is, the cylindrical bore 48 eliminates a planar surface which may otherwise be contacting the grouting material 106 that is substantially flush to the neck portion 74 of the host femur 68.

To remove the positioning jig 36, the positioning jig 36 is simply pivoted out from the hip prosthesis 108, as shown clearly in FIG. 7G. In other words, the positioning jig 36 is pivoted from the first surface or landmark 102 as the nesting surface 52 is slid slightly upward along the head 114 and away from the head 114 with the second mating surface 44 finally separating from the first mating surface 102 within the host femur 68. As the positioning jig 36 is pivoted away from the hip prosthesis 108, the notch region 54 defined by the wall 56 and the wall 58 enables the positioning jig 36 to be pivoted upward and outward away from the neck 112 and the head 114 as the "V" shaped slot 60 separates from the neck 112.

While the cutter 10 and the positioning jig 36 are described in detail in connection with the hip prosthesis 108, those skilled in the art will recognize that the cutter 10 and the positioning jig 36 can be utilized with various other orthopedic implants inserted within various bones. Moreover, while the cavity 76 is discussed above as being formed with the reamer 80 and the rasp 86, the positioning jig 36 can be utilized in conjunction with a programmable cutting device such as a robot or mill which could be used to form the cavity 76, as well as the first mating surface or landmark 102.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention.

What is claimed is:

1. A set of surgical instruments for positioning a prosthesis within a cavity in a bone, said set comprising:
   said prosthesis having a distal end, a medial body and a proximal end, said distal end and said medial body operable to be inserted into the cavity in the bone;
   means for establishing a first three-dimensional mating surface in the bone; and
   means for positioning said distal end and said medial body of said prosthesis within the cavity in the bone, said means for positioning having a second three-dimensional mating surface and a third surface, said second three-dimensional mating surface being adapted to substantially removably nest with said first three-dimensional mating surface in the bone and said third surface being adapted to removably engage said proximal end of the prosthesis adjacent to said medial body, said prosthesis being located at a predetermined position relative to the cavity in the bone when said second three-dimensional mating surface substantially nests with said first three-dimensional mating surface and said third surface engages said proximal end of the prosthesis adjacent to said medial body, whereby upon securing said prosthesis within the cavity in the bone, said means for positioning said prosthesis is removed from said first three-dimensional mating surface in the bone and said proximal end of said prosthesis.

2. The apparatus as defined in claim 1 wherein said means for establishing a first three-dimensional mating surface in the bone includes a cutter adapted to establish said first three-dimensional mating surface in the bone.

3. The apparatus as defined in claim 2 wherein said cutter includes a single blade cutting member for establishing said first three-dimensional mating surface in the bone.

4. The apparatus as defined in claim 2 wherein said means for establishing a first three-dimensional mating surface in the bone further includes a plug member operable to be inserted into the cavity in the bone, said cutter engaging a reference member of said plug member as said cutter establishes said first three-dimensional mating surface in the bone.

5. An apparatus for positioning a prosthesis within a cavity in a bone, said apparatus comprising:
   means for establishing a first three-dimensional mating surface in the bone, said means for establishing a first three-dimensional mating surface in the bone includes a rasp operable to form the cavity in the bone and a cutter operable to engage a reference member of said rasp and having a three-dimensional cutting surface, said three-dimensional cutting surface establishes said first three-dimensional mating surface in the bone; and
   means for positioning the prosthesis within the cavity in the bone, said means for positioning having a second mating surface and a third surface, said second mating surface being adapted to substantially mate with said first three-dimensional mating surface in the bone and said third surface being adapted to engage the prosthesis, whereby said prosthesis is positioned relative to the cavity in the bone when said second mating surface substantially mates with said first three-dimensional mating surface and said third surface engages the prosthesis.

6. An apparatus for positioning a prosthesis within a cavity in a bone, said apparatus comprising:
   means for establishing a first mating surface in the bone; and
   means for positioning the prosthesis within the cavity in the bone, said means for positioning having a second mating surface and an axially extending slot operable to removably engage the prosthesis, said second mating surface being adapted to substantially mate with said first mating surface in the bone and said axially extending slot being adapted to removably engage the prosthesis, whereby said prosthesis is positioned relative to the cavity in the bone when said second mating surface substantially sates with said first mating surface and said axially extending slot engages the prosthesis.

7. The apparatus as defined in claim 1 wherein the cavity has a first sidewall and the prosthesis has a second sidewall, said means for positioning substantially centers a portion of the prosthesis within the cavity in the bone, whereby the first sidewall is positioned substantially away from the second sidewall with a cement mantel there between.

8. A set of surgical instruments for positioning a hip prosthesis in a cavity of an intramedullary canal of a host femur, said set comprising:
   said hip prosthesis having a distal end and a proximal end, said distal end of said hip prosthesis operable to be inserted into the cavity of the intramedullary canal;
   a plug member operable to be inserted into the cavity of the intramedullary canal;
   a cutter having a three-dimensional cutting surface and adapted to engage said plug member, said cutter operable to create a first three-dimensional mating surface in the host femur with said three-dimensional cutting surface; and
   a positioning jig having a second three-dimensional mating surface and a third surface, said second three-dimensional mating surface adapted to substantially removably nest with said first three-dimensional mating surface in the host femur and said third surface adapted to removably engage said proximal end of said hip prosthesis, a portion of said hip prosthesis being substantially positioned centrally within the cavity of the intramedullary canal of the host femur when said second three-dimensional mating surface substantially nests with said first three-dimensional mating surface and said third surface engages said proximal end of said hip prosthesis, whereby upon securing said portion of said hip prosthesis substantially centrally within the cavity of the intramedullary canal of the host femur, said positioning jig is removed from said first three-dimensional mating surface in the host femur and said proximal end of said hip prosthesis.

9. A set of surgical instruments for positioning a hip prosthesis in a cavity of an intramedullary canal of a host femur, said set comprising:

said hip prosthesis operable to be inserted into the cavity of the intramedullary canal;

a plug member operable to be inserted into the cavity of the intramedullary canal, said plug member is a rasp operable to form the cavity in the intramedullary canal;

a cutter having a three-dimensional cutting surface and adapted to engage said plug member, said cutter operable to create a first mating surface in the host femur with said three-dimensional mating surface; and a positioning jig having a second mating surface and a third surface, said second mating surface adapted to substantially mate with said first mating surface in the host femur and said third surface adapted to engage said hip prosthesis, whereby a portion of said hip prosthesis is substantially positioned centrally within the cavity of the intramedullary canal of the host femur when said second mating surface substantially mates with said first mating surface and said third surface engages said hip prosthesis.

10. The set of surgical instruments as defined in claim 8 wherein said plug member includes a removable handle and a reference member, said cutter is adapted to operably engage said reference member when said handle is removed.

11. The set of surgical instruments as defined in claim 10 wherein said reference member is operable with said cutter to limit the depth of said first three-dimensional mating surface created in the host femur.

12. The set of surgical instruments as defined in claim 8 wherein said cutter includes a single blade cutting member operable to cut said first three-dimensional mating surface into the host femur.

13. The set of surgical instruments as defined in claim 8 wherein said third surface of said positioning jig defines an axially extending slot adapted to removably engage a neck portion of said proximal end of said hip prosthesis.

14. The set of surgical instruments as defined in claim 13 wherein said positioning jig includes a fourth surface defining a nesting location for receiving a portion of a head of said proximal end of said hip prosthesis.

15. The set of surgical instruments as defined in claim 13 wherein said positioning jig defines a notched portion adjacent to said axially extending slot operable to enable the removal of said positioning jig from said hip prosthesis after said hip prosthesis is substantially centrally positioned within the cavity of the intramedullary canal of the host femur.

16. The set of surgical instruments as defined in claim 8 wherein said first three-dimensional mating surface in the host femur is a substantially angled concave surface and said second three-dimensional mating surface of said positioning jig is a substantially angled convex surface adapted to substantially mate with the substantially concave surface.

17. The set of surgical instruments as defined in claim 8 wherein said positioning jig includes a cylindrical bore and an annular seat adjacent said second three-dimensional mating surface for assisting in the removal of said positioning jig from said first three-dimensional mating surface.

18. A method for positioning a hip prosthesis in a cavity of an intramedullary canal of a host femur, said method comprising the steps of:

providing a hip prosthesis having a first sidewall;

forming a cavity in the intramedullary canal having a second sidewall and operable to receive a portion of the hip prosthesis;

forming a three-dimensional landmark in the host femur at a predetermined position relative to the cavity in the intramedullary canal;

delivering a grouting material into the cavity of the intramedullary canal;

providing a positioning jig having a first surface adapted to removably engage the hip prosthesis and a second three-dimensional surface adapted to removably nest with the three-dimensional landmark;

positioning the portion of the hip prosthesis within a predetermined location in the cavity of the intramedullary canal where the first sidewall is positioned substantially away from the second sidewall by removably nesting the second three-dimensional surface of the positioning jig with the three-dimensional landmark and removably engaging the hip prosthesis with the first surface of the positioning jig; and removing the positioning jig from the three-dimensional landmark and the hip prosthesis upon securing the portion of the hip prosthesis within the pedetermined location in the cavity of the intramedullary canal of the host femur with the grouting material Positioned substantially between the first sidewall And the second sidewall.

19. The method as defined in claim 18 wherein the step of forming the three-dimensional landmark in the host femur includes the steps of:

inserting a rasp in the cavity of the intramedullary canal; and engaging a portion of the rasp with a rotating cutter to establish the three-dimensional landmark in the host femur.

20. The method as defined in claim 18 wherein the step of providing a positioning jig further includes the step of providing an axially extending slot in the positioning jig adapted to removably engage a neck portion of the hip prosthesis.

* * * * *

UNITED STATES PATENT AND TRADEMARK OFFICE
CERTIFICATE OF CORRECTION

PATENT NO.    : 5,885,295
DATED         : March 23, 1999
INVENTOR(S)   : John McDaniel, et al.

It is certified that error appears in the above-identified patent and that said Letters Patent is hereby corrected as shown below:

Column 3,
Line 59, "cutter" should be -- cutting --.

Claims,
Column 8, claim 6,
Line 41, "sates" should be -- mates --.

Column 10, claim 18,
Line 42, "Positioned" should be -- positioned --.
Line 43, "And" should be -- and --.

Signed and Sealed this

Twenty-third Day of October, 2001

Attest:

*Nicholas P. Godici*

NICHOLAS P. GODICI
*Attesting Officer*   *Acting Director of the United States Patent and Trademark Office*